United States Patent [19]

Richman

[11] Patent Number: 4,465,582

[45] Date of Patent: Aug. 14, 1984

[54] CONTINUOUS FLOW ELECTROPHORESIS APPARATUS

[75] Inventor: David W. Richman, Chesterfield, Mo.

[73] Assignee: McDonnell Douglas Corporation, Long Beach, Calif.

[21] Appl. No.: 380,976

[22] Filed: May 24, 1982

[51] Int. Cl.³ ............................................. G01N 27/28
[52] U.S. Cl. ................................................ 204/299 R
[58] Field of Search ....................... 204/299 R, 180 R

[56] References Cited

U.S. PATENT DOCUMENTS

| | | | |
|---|---|---|---|
| 4,061,560 | 12/1977 | Hannig et al. | 204/180 R |
| 4,309,268 | 1/1982 | Richman | 204/301 |
| 4,394,246 | 7/1983 | Richman et al. | 204/301 |

Primary Examiner—John F. Niebling
Assistant Examiner—B. J. Boggs, Jr.
Attorney, Agent, or Firm—Gregory A. Cone; George W. Finch; Donald L. Royer

[57] ABSTRACT

The unique construction of this Continuous Flow Electrophoresis Apparatus eliminates the need for ion permeable membranes between the electrode chambers at the sides of the separation chamber and the separation chamber itself. By carefully controlling the relative geometries of the electrode chambers and the separation chamber, a membrane-less electrophoresis separation may be conducted without the problems attendant to these chambers which utilize ion permeable membranes.

6 Claims, 4 Drawing Figures

CONTINUOUS FLOW ELECTROPHORESIS APPARATUS

BACKGROUND OF THE INVENTION

1. Field of the Invention

The present invention relates to an apparatus for performing a continuous free flow electrophoresis process. More particularly, the present invention relates to an apparatus for performing a continuous free flow electrophoresis procedure which is constructed such that there are no ion permeable membranes between the electrode chambers and the central separation chamber.

2. Description of the Prior Art

Electrophoresis, in general, is the phenomenon of the migration of charged particles or ions in a liquid carrier medium under the influence of an electric field. This phenomenon can be used to separate small particles which, by reason of different surface chemical properties, exhibit different concentrations of surface charge in the given medium. Under the influence of the electrical field, the electrophoretic mobilities of the various classes of charged particles in the carrier medium will be different. A sample continuously introduced at some point into the sheet of liquid carrier medium (buffer) flows in a narrow band in the absence of a potential gradient; however, when the potential gradient is applied to the sheet of buffer, the sample particles are separated under the influence of the electrical field into various particle groups or components depending upon the electrophoretic mobility of the respective particles, the strength of the field, and the length of time that the particles remain in the field. Particles of similar mobility are concentrated in distinctive zones or bands which fan out from the point of sample introduction.

The present invention relates in particular to free flow continous electrophoresis in which a buffer solution is made to flow freely in a uniform film or sheet through a chamber defined by two parallel enlongate plates. A sample is introduced into the buffer sheet at some point, and an electric potential gradient is applied across this flowing sheet perpendicular to the direction of buffer flow. The individual components within each sample then separate into narrow bands, depending upon their respective electrophoretic mobilities, and can be collected from the outlet end of the electrophoresis chamber through one or more of a plurality of small tubes disposed along a collection manifold at the outlet of the chamber.

In the present art, the electrical field is established between a pair of electrodes, one at each side of the separation chamber. Because the carrier fluid or buffer is normally water plus ionic species added to protect the viability of the biological material being separated, the buffer fluid is electrically conductive. When the electrical field is imposed upon the conductive buffer carrier fluid, electrolysis of the water occurs, liberating hydrogen gas at the cathode electrode and oxygen gas at the anode electrode. Since the amount of gas liberated usually exceeds the amount that can be dissolved in the carrier buffer flow, undesirable by-products are introduced into the buffer flow stream. These undesirable by-products cause instability affecting separation and should not be allowed to contaminate the buffer flow. To this end, conventional free flow electrophoresis separation apparatus are universally constructed with ion permeable membranes or ion exchange membranes separating the electrode chambers from the central separation chamber. The use of such membranes by no means renders the apparatus ineffective; however, the use of membranes does place substantial limitations upon the separation process. First, polarization of the membranes under the influence of the electric field causes variations in the population densities of the various ionic species contained within the separation chamber. Also, heating of the carrier (buffer) fluid is increased due to the resistance of the ion permeable membranes to the flow of electrical current through them. Further, pressure differentials across the ion permeable membranes are introduced by the mechanism of electro-osmotic pumping.

SUMMARY OF THE INVENTION

The apparatus of this invention comprises a novel continuous free flow electrophoresis separation apparatus constructed such that there are no membranes separating the electrode chambers from the central separation chamber. The apparatus requires a physical configuration such that there is sufficient buffer flow in the vicinity of the electrode chambers to transport the products of electrolysis within the electrode chambers at a neglible pressure gradient between the local electrode chamber flow and the buffer flow within the central separation chamber. It is also highly advantageous to include means for controlling the electrode buffer flow such that the inlet and outlet flows for each electrode chamber are fixed in relationship and, further, that the total electrode buffer flow out equals the total electrode buffer flow into the apparatus.

DETAILED DESCRIPTION OF THE INVENTION

A continuous free flow electrophoresis separation procedure is a process which finds application in separating out the various components of a sample stream composed of various different proteins, cells, or other particles, each such component having a particular surface electrical charge and viscous drag cross section. The sample stream is introduced into a buffer filled electrophoresis separation chamber in which the buffer and the introduced sample are continuously circulated from the inlet to the outlet of the separation chamber. The buffer solution is designed to maintain the viability of the samples over the course of the separation procedure. The electrical field is applied across the separation chamber flow in the direction of the desired separation.

The design of the central separation chamber portion of the electrophoresis apparatus of this invention is conventional, and the reader is referred to U.S. Pat. No. 4,309,268 issued to the present inventor on Jan. 5 1982, which is incorporated by reference herein in its entirety. The electrophoresis separation chamber itself is defined by two flat parallel rectilinear plates separated by a distance b and having a length, x. In order to dispense with the ion permeable membranes found in conventional electrophoresis apparatus, the electrode buffer chambers, located at the lateral edges of the central separation chamber, are constructed such that their cross sectional area will support a volume flow rate sufficient to remove substantially all of the electrolysis by-products from the apparatus without the introduction of these by-products into the central separation chamber. To this end, the desired electrode buffer flow rate in each of these lateral electrode chambers is about an order of magnitude greater than is the buffer flow rate within the central separation chamber. The embodiment discussed in detail below develops a configuration in which the lateral electrode buffer chambers have a circular cross section.

Figure 1:
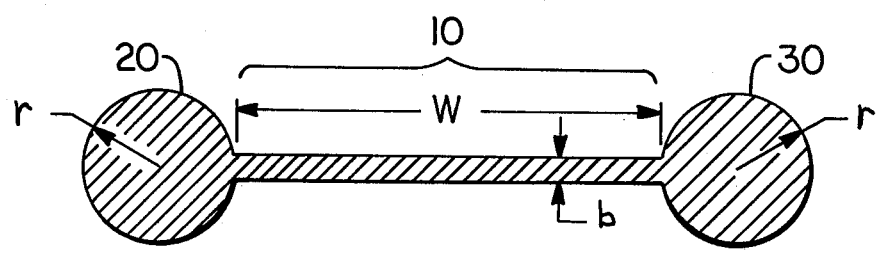
FIG. 1 is a cross section of the lateral electrode chambers and the central separation chamber of one embodiment of this invention.
Figure 2:
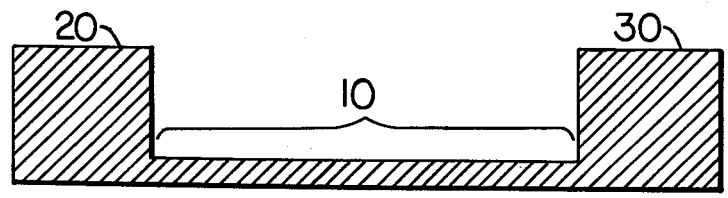
FIGS. 2 and 3 are cross-sectional views of alternate embodiments of this invention.
Figure 3:
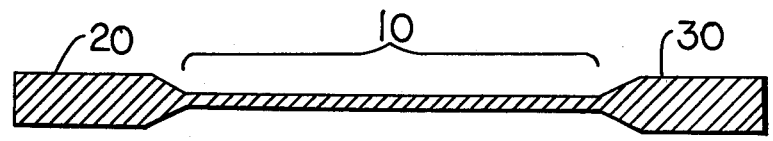

However, it should be realized that a vast variety of differently shaped lateral electrode buffer chambers may be employed to the same end without departing from the spirit of this invention. FIG. 1, then, shows a cross sectional view of the lateral electrode buffer chambers in conjunction with the central separation chambers in which the lateral electrode buffer chambers assume a circular cross section. However, in FIG. 2 is shown an alternate embodiment in which the lateral electrode buffer chambers assume a square cross section. In FIG. 3 an elongated cross section has been used for the electrode buffer chambers. This and other elongated shapes have the advantage that the ratio of flow area to hydraulic diameter (four times the area divided by the wetted perimeter) is greater than that for regular polygons. Therefore, the electrode chamber flow can be increased over that for a regular polygon before turbulent flow occurs in the passage. The cross sectional configurations of the electrode buffer filled chambers could, of course, assume other shapes as well. To repeat, the important concept is that the volumetric relationships of the chambers are such that the flow rate within the electrode buffer chambers allows substantially none of the electrolysis by-products from the electrode buffer chambers into the central separation chamber.

Returning to the embodiment shown in cross sectional view in FIG. 1, the apparatus consists of a separation chamber 10 bounded on its lateral edges by a first electrode buffer chamber 20 and a second electrode buffer chamber 30. The separation chamber itself is defined by two closely spaced parallel plates separated by a distance b and having a width w. The effective length of the apparatus chambers is x, not shown. The lateral electrode buffer chambers are right circular cylinders, each having a radius r.

The following discussion will mathematically develop the relative dimensions for this embodiment such that there is negligible pressure gradient between the lateral electrode buffer chambers and the central separation chamber.

For fully developed laminar flow within a tube, the pressure gradient is:

$$\frac{dp}{dx}\Big]_{tube} = \mu V \left(\frac{-4}{r^2}\right)$$

where:
p=pressure, dynes
x=length, cm
$\mu$=viscosity, poise
V=centerline velocity, cm/sec
r=tube radius, cm And the mass flow rate is:

$$\overset{\circ}{m}_e = \frac{\rho}{2} \pi r^2 V$$

where:
$\overset{\circ}{m}_e$=electrode mass flow rate, gm/sec
$\rho$=density, gm/cm$^3$
Substituting, we have:

$$\frac{dp}{dx}\Big]_{tube} = \mu \left(\frac{2 \overset{\circ}{m}_e}{\rho \pi r^2}\right)\left(\frac{-4}{r^2}\right)$$

$$= \frac{-8\mu \overset{\circ}{m}_e}{\pi \rho r^4}$$

For fully developed laminar flow between infinite parallel plates, the pressure gradient is:

$$\frac{dp}{dx}\Big]_{plates} = \mu V\left(\frac{-8}{b^2}\right)$$

where:
V=centerline velocity, cm/sec
b=plate spacing, cm
And the mass flow rate for finite width parallel plates is:

$$\overset{\circ}{m}_c = \tfrac{2}{3} \rho b w V$$

where
$\overset{\circ}{m}_c$=carrier mass flow rate, gm/sec
w=plate width, cm
Substituting, we have:

$$\frac{dp}{dx}\Big]_{plates} \simeq \mu \frac{3 \overset{\circ}{m}_c}{2 \rho b w}\left(\frac{-8}{b^2}\right)$$

$$\simeq \frac{-12 \mu \overset{\circ}{m}_c}{\rho w b^3}$$

The approximate sign accounts for the plates being much wider than the plate spacing rather than infinite in width.

Now for equal pressure gradients with length we have:

$$\frac{-8}{\pi} \frac{\mu \overset{\circ}{m}_e}{\rho r^4} \simeq \frac{-12 \mu \overset{\circ}{m}_c}{\rho w b^3}$$

And the radius of the electrode buffer flow chamber is:

$$r \simeq \sqrt[4]{\frac{2 w b^3}{3 \pi} \frac{\overset{\circ}{m}_e}{\overset{\circ}{m}_c}}$$

Similar logic can be applied to find suitable geometry for electrode flow chambers of any shape, e.g., triangles, squares, or rectangles, with the consideration that the path length between the electrode and the lateral edges of the separation is minimized, and the electrode flow is substantially between the electrode and the lateral edge of the carrier buffer flow passage.

Figure 4:
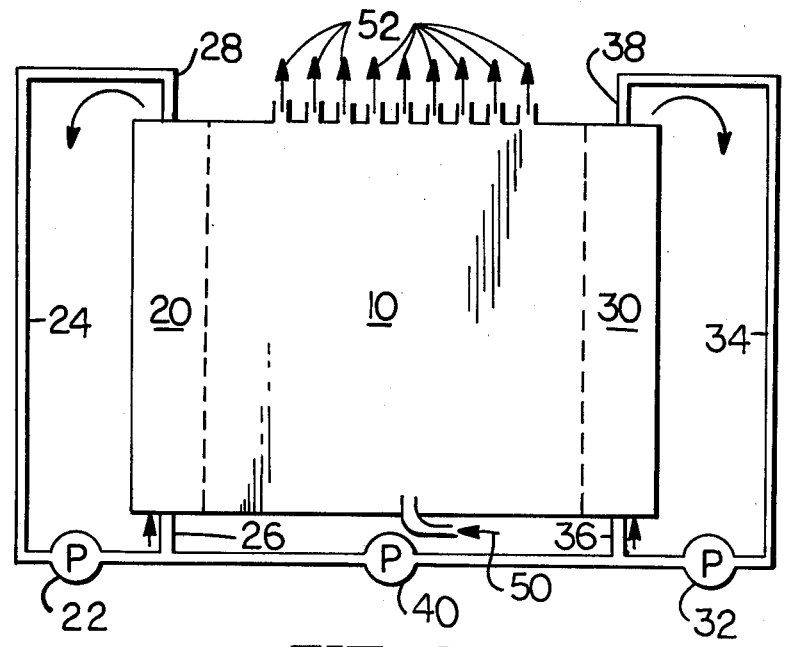
FIG. 4 is a diagramatic view showing one arrangement for electrode buffer flow control showing a pump layout for one embodiment of this invention.

As was mentioned above, it is necessary to employ means for controlling the relationship of each of the buffer electrode flows into each chamber with respect to its respective exit flow. One such configuration is shown in FIG. 4 in which the electrophoresis apparatus with its central separation chamber 10 and first 20 and second 30 lateral electrode buffer chambers. The inlet 26 to the first electrode buffer chamber 20 and outlet 28 are connected by a piping run 24, and buffer is conducted through this fixed volume loop by the action of a pump 22. In a similar fashion, the inlet 36 to the second electrode buffer chamber 30 and the outlet 38 are connected by a piping run 34 into a second fixed volume loop; and buffer is forced through this loop by the action of a second pump 32. Since each loop is a fixed volume loop, and, therefore, the flow into each pump must equal the flow leaving each pump, the flow into each electrode flow buffer chamber must equal the flow leaving each electrode buffer chamber. If an added component flow across the separation chamber 10 is desired for purposes of crescent distortion control (covered in detail in U.S. Pat. No. 4,309,268), this added flow component can be implemented by an added optional pump 40 between the two electrode buffer loops 24 and 34. For such purposes, the pump flow rate through the pump 40 would be implemented to equal the desired crescent distortion control cross chamber flow component in the central separation chamber 10, but in an opposite direction. For such purposes, this optional pump 40 could as easily be placed across the outlets of the apparatus 28 and 38. It should be realized that this introduced cross chamber flow is small in relation to the electrode buffer flow rate and would not cause significant amounts of the electrolysis by-products to enter the separation chamber. Also shown in FIG. 4, are a portion of the inlet manifold assembly means 50 and the collection manifold assembly means 52. That portion of the inlet manifold shown is the tube through which the unseparated sample is introduced into the separation; not shown are a plurality of other inlet tubes through which buffer solution only is introduced into the central separation chamber. The multiplicity of outlet tubes labeled 52 at the top of the central separation chamber comprise the outlet collection manifold assembly means. Actually the number of individual outlet tubes which are individually collected in collection means not shown, may number over 100 depending on the precision of the separation.

This particular method of controlling the inlet and outlet flow rates for each electrode buffer chamber should not be considered as limitative. For example, pumps on both the outlet and inlet to each electrode buffer chamber could be controlled to the desired flow rates. Additionally, flow rates could be similarly controlled by utilizing remote buffer reservoirs in which the heights of the stored buffer solution in the reservoirs are precisely controlled to achieve the same flow rates as in the previously discussed arrangements.

I claim as my invention:

1. In a free flow electrophoresis separation apparatus comprising:

a rectilinear, buffer filled separation chamber defined by two elongated, spaced apart, parallel plates forming a front and a back to the chamber, an end comprising a collection manifold assembly means, an end comprising inlet manifold assembly means, and two sides;

two buffer filled electrode chambers, one electrode chamber disposed adjacent to one side of the separation chamber and the second electrode chamber disposed adjacent to the other side of the separation chamber;

at least one sample inlet port located at or near the inlet manifold assembly means wherein an electrical field is applied across the separation chamber by oppositely charged electrodes within the electrode chambers wherein are formed electrolysis by-products; and means to cause the buffer fluid to flow through the apparatus;

the improvement comprising:

a construction of the apparatus such that the sides of the separation chamber open unobstructedly into the electrode chambers and such that the cross sectional area of each electrode chamber relative to the cross sectional area of the separation chamber is sufficient to support a buffer flow rate which effectively confines electrolysis by-products created at the electrodes to the elecrode chambers.

2. The apparatus of claim 1 wherein the electrode chamber buffer flow rate is fixed in relationship to the separation chamber buffer flow rate so that there is no substantial pressure differential between the separation chamber and an electrode chamber under conditions wherein there is no pressure differential between the two electrode buffer chambers when buffer is pumped through the apparatus.

3. The apparatus of claim 1 wherein the volume of each electrode chamber and the buffer-contacted surface area of the electrode within each chamber are sufficient to assure that the electrolysis by-products are at least substantially in the buffer with the buffer remaining in a less than saturated condition from the electrolysis by-products.

4. The apparatus of claim 1 wherein the shape of each electrode chamber is such that the flow within the chamber remains laminar at the operational flowrate.

5. The apparatus of claim 1 further comprising means for controlling the flow of buffer within an electrode chamber such that the flow into the chamber is substantially equal to the flow leaving the chamber.

6. In a free flow electrophoresis separation apparatus comprising:

a rectilinear, buffer filled separation chamber defined by two elongated, spaced apart, parallel plates forming a front and a back to the chamber, an end comprising a collection manifold assembly means, an end comprising inlet manifold assembly means, and two sides;

two buffer filled electrode chambers, one electrode chamber disposed adjacent to one side of the separation chamber and the second electrode chamber disposed adjacent to the other side of the separation chamber;

At least one sample inlet port located at or near the inlet manifold assembly means wherein an electrical field is applied across the separation chamber by oppositely charged electrodes within the electrode chambers wherein are formed electrolysis by-products; and means to cause the buffer fluid to flow through the apparatus;

the improvement comprising:

a construction of the apparatus such that the sides of the separation chamber open unobstructedly into the electrode chambers and such that the cross sectional area of each electrode chamber relative to the cross sectional area of the separation chamber is sufficient to support a buffer flow rate which effectively confines electrolysis by-products created at the electrodes to the electrode chambers and wherein the apparatus further comprises means for controlling the flow of buffer within an electrode chamber such that the flow into the chamber is substantially equal to the flow leaving the chamber, such means comprising fluid conduit means connecting an outlet of an electrode chamber with an inlet to the same electrode chamber in combination with pump means.

* * * * *